United States Patent
Terman

(10) Patent No.: US 6,180,097 B1
(45) Date of Patent: Jan. 30, 2001

(54) METHOD OF CANCER TREATMENT

(76) Inventor: David S. Terman, P.O. Box 987, Pebble Beach, CA (US) 93953

( * ) Notice: Under 35 U.S.C. 154(b), the term of this patent shall be extended for 0 days.

(21) Appl. No.: 09/183,437

(22) Filed: Oct. 30, 1998

Related U.S. Application Data

(63) Continuation of application No. 08/491,746, filed on Jun. 19, 1995, which is a continuation of application No. 08/189,424, filed on Jan. 31, 1994, now Pat. No. 5,728,388, which is a continuation-in-part of application No. 08/025,144, filed on Mar. 2, 1993, now abandoned, which is a continuation-in-part of application No. 07/891,718, filed on Jun. 1, 1992, now abandoned, and a continuation-in-part of application No. PCT/US91/00342, filed on Jan. 17, 1991, which is a continuation-in-part of application No. 07/466,577, filed on Jan. 17, 1990, now abandoned, which is a continuation-in-part of application No. 07/416,530, filed on Oct. 3, 1989, now abandoned.

(51) Int. Cl.$^7$ .......................... A01N 63/00; C07H 21/04; C12N 15/85; C12N 15/09; A61K 48/00
(52) U.S. Cl. .................. 424/93.1; 424/93.21; 435/320.1; 435/325; 435/455; 536/235
(58) Field of Search ............................. 425/93.1, 93.21; 435/320.1, 325.1, 455

(56) References Cited

PUBLICATIONS

Chen L et al., "Costimulation of Antitumor Immunity by the B7 Counterreceptor for the T Lymphocyte Molecules CD28 and CTLA–4," *Cell* 71:1093–1102 (1992).

Damle NK et al., "Proliferation of Human T Lymphocytes Induced with Superantigens is Not Dependent on Costimulation by the CD28 Counter–Receptor B7," *J. of Immunology* 150(3):726–735 (1993).

Dohlsten M et al., "Role the Adhesion Molecule ICAM–1 (CD54) in Staphylococcal Enterotoxin–Mediated Cytotoxicity," *Eur. J. Immunol.* 21:131–135 (1991).

Gimmi CD et al., "B–Cell Surface Antigen B7 Provides a Costimulatory Signal That Induces T Cells to Proliferate and Secrete Interleukin 2," *Proc. Natl. Acad. Sci. USA* 88:6575–6579 (1991).

Green JM et al., "CD28 and Staphylococcal Enterotoxins Synergize to Induce MHC–Independent T–Cell Proliferation," *Cellular Immunology* 145:11–20 (1992).

Mittrucker H and Fleischer B, "Stimulator Cell–Dependent Requirement for CD2– and LFA–1–Mediated Adhesions in T Lymphocyte Activation by Superantigenic Toxins," *Cellular Immunology* 139:108–117 (1992).

Ostrand–Rosenberg S et al., "Rejection of Mouse Sarcoma Cells After Transfection of MHC Class II Genes," *J. of Immunology* 144:4068–4071 (1990).

Townsend SE and Allison JP, "Tumor Rejection After Direct Costimulation of CD8$^+$ T Cells by B7–Transfected Melanoma Cells," *Science* 259:368–370 (1993).

*Primary Examiner*—Geetha P. Bansal
(74) *Attorney, Agent, or Firm*—Shmuel Livnat Rader Fishman &Grauer PLLC

(57) ABSTRACT

Treatment of solid tumors, including their metastases, without radiation, surgery or standard chemotherapeutic agents is described. Ex vivo stimulation of cells, selection of specific Vβ subsets of stimulated cells and reinfusion of the Vβ subsets of stimulated cells is employed for cancer therapy.

25 Claims, 3 Drawing Sheets

METHOD OF CANCER TREATMENT

RELATED APPLICATION DATA

This application is a continuation of U.S. application Ser. No. 08/491,746, filed Jun. 19, 1995; which is a continuation of U.S. application Ser. No. 08/189,424, filed Jan. 31, 1994; (U.S. Pat. No. 5,728,388) which is a continuation-in-part of U.S. application Ser. No. 08/025,144, filed Mar. 2, 1993 (abandoned); which is a continuation-in-part of U.S. application Ser. No. 07/891,718, filed Jun. 1, 1992 (abandoned) and a continuation-in-part of Ser. No. PCT/US91/00342, filed Jan. 17, 1991; which is a continuation-in-part of U.S. application Ser. No. 07/466,577, filed Jan. 17, 1990 (abandoned); which is a continuation-in-part of U.S. application Ser. No. 07/416,530, filed Oct. 3, 1989 (abandoned).

FIELD OF THE INVENTION

The invention generally relates to the treatment of cancer, and, more specifically, to the treatment of solid tumors, including their metastases, without radiation, surgery or standard chemotherapeutic agents.

BACKGROUND

Therapy for cancer has largely involved the use of radiation, surgery and chemotherapeutic agents. However, results with these measures, while beneficial in some tumors, has had only marginal or no effect in many others. Furthermore, these approaches have often unacceptable toxicity.

Both radiation and surgery suffer from the same theoretical drawback. It has been recognized that, given that a single clonogenic malignant cell can give rise to sufficient progeny to kill the host, the entire population of neoplastic cells must be eradicated. See generally, Goodman and Gilman *The Pharmacological Basis of Therapeutics* (Pergamon Press, 8th Edition) (pp. 1202–1204). This concept of "total cell kill" implies that total excision of a tumor is necessary for a surgical approach, and complete destruction of all cancer cells is needed in a radiation approach, if one is to achieve a cure. In practice this is rarely possible; indeed, where there are metastases, it is impossible.

The term "chemotherapy" simply means the treatment of disease with chemical substances. The father of chemotherapy, Paul Ehrlich, imagined the perfect chemotherapeutic as a "magic bullet;" such a compound would kill invading organisms without harming the host. This target specificity is sought in all types of chemotherapeutics, including anticancer agents.

However, specificity has been the major problem with anticancer agents. In the case of anticancer agents, the drug needs to distinguish between host cells that are cancerous and host cells that are not cancerous. The vast bulk of anticancer drugs are indiscriminate at this level. Typically anticancer agents have negative hematological effects (e.g., cessation of mitosis and disintegration of formed elements in marrow and lymphoid tissues), and immunosuppressive action (e.g., depressed cell counts), as well as a severe impact on epithelial tissues (e.g., intestinal mucosa), reproductive tissues (e.g., impairment of spermatogenesis), and the nervous system. P. Calabresi and B. A. Chabner, In: Goodman and Gilman *The Pharmacological Basis of Therapeutics* (Pergamon Press, 8th Edition) (pp. 1209–1216).

Success with chemotherapeutics as anticancer agents has also been hampered by the phenomenon of multiple drug resistance, resistance to a wide range of structurally unrelated cytotoxic anticancer compounds. J. H. Gerlach et al., *Cancer Surveys*, 5:25–46 (1986). The underlying cause of progressive drug resistance may be due to a small population of drug-resistant cells within the tumor (e.g., mutant cells) at the time of diagnosis. J. H. Goldie and Andrew J. Coldman, *Cancer Research*, 44:3643–3653 (1984). Treating such a tumor with a single drug first results in a remission, where the tumor shrinks in size as a result of the killing of the predominant drug-sensitive cells. With the drug-sensitive cells gone, the remaining drug-resistant cells continue to multiply and eventually dominate the cell population of the tumor.

Treatment at the outset with a combination of drugs was proposed as a solution, given the small probability that two or more different drug resistances would arise spontaneously in the same cell. V. T. DeVita, Jr., *Cancer*, 51:1209–1220 (1983). However, it is now known that drug resistance is due to a membrane transport protein, "P-glycoprotein," that can confer general drug resistance. M. M. Gottesman and I. Pastan, *Trends in Pharmacological Science*, 9:54–58 (1988). Phenotypically, the tumor cells show, over time, a reduced cellular accumulation of all drugs. In short, combination chemotherapy appears not to be the answer.

What is needed is a specific anticancer approach that is reliably tumoricidal to a wide variety of tumor types. Importantly, the treatment must be effective with minimal host toxicity.

SUMMARY OF THE INVENTION

The invention generally relates to the treatment of cancer, and, more specifically, to the treatment of solid tumors, including their metastases, without radiation, surgery or standard chemotherapeutic agents. In one embodiment, the invention involves using superantigens, including SEA and SEB, to stimulate tumor draining lymph node cells ex vivo, allowing them to differentiate into tumor specific immune effector cells. The cells are then reintroduced into the same host to mediate anticancer therapeutic effects. In another embodiment, the stimulated cells are introduced into a different host. In still a third embodiment, the cells are established as a cell line for continuous anticancer use.

In one embodiment, lymphocytes are obtained early in life from cancer-free hosts. The cells are stored in appropriate containers under liquid nitrogen using conventional techniques (e.g., DMSO, culture media, fetal calf serum, etc.) until the onset of disease. At this point, the cells may be thawed, and cultured and stimulated in the manner of the present invention for reinfusion.

Alternatively, an established cell line may be made from cancer-free hosts. The cell line can be stored as above. On the other hand, they may be passed continuously in culture until use.

The ex vivo stimulation method has decided advantages over direct intravenous injection of superantigens, namely: 1) the superantigens are ensured of contacting their appropriate target cell, namely, T lymphocytes; in other words, stimulation is specific; 2) stimulation in culture allows for the removal of the stimulating antigens prior to reintroduction of the cells in the host, i.e., the host is exposed to only very small amounts of superantigens in vivo; and 3) lack of systemic exposure to the stimulating antigens precludes significant interference with naturally occurring or induced antibodies to superantigens.

The present invention demonstrates that superantigens can reliably produce tumoricidal reactions to a wide variety of tumor types. Moreover, success is achieved with minimal host toxicity using the in vitro sensitization technique.

In its simplest form, the present invention offers a method for inducing a tumoricidal reaction in vivo comprising contacting cells with superantigens ex vivo and infusing them into a tumor-bearing host. The cells are typically hematopoietic cells, such as peripheral blood lymphocytes, spleen cells, tumor-infiltrating lymphocytes or lymph node cells. Where they are lymph node cells, it is preferred that they are from a tumor-bearing host. The superantigens may comprise enterotoxins of *Staphylococcus aureus*, or synthetic polypeptides with substantial structural homology and statistically significant sequence homology to natural superantigens.

The present invention offers a method of human cancer treatment comprising: a) providing a human cancer patient; b) obtaining hematopoietic cells from said patient; c) contacting said cells ex vivo with one or more superantigens to generate stimulated cells; and d) re-introducing said stimulated cells into said patient so as to induce an in vivo therapeutic, tumoricidal reaction. Preferably the hematopoietic cells are cultured in culture media containing enterotoxins and the cultured cells are washed prior to re-introducing said stimulated cells into said patient so as to essentially avoid introducing enterotoxins in vivo.

The culture cells can be viewed as a reagent for treating cancer, comprising T cells sensitized to a growing tumor and stimulated with superantigens. Preferably, the T cells are suspended in media suitable for intravenous administration to a human cancer patient, such as a media comprising a physiological buffered saline solution.

While not limited to any mechanism, it is believed that culturing the cells in the manner proposed results in subset enrichment. In this regard, the present invention provides a method of human cancer treatment comprising: a) providing a human cancer patient, having one or more growing tumors; b) obtaining Vβ-expressing T cells from said patient that are sensitized to said growing tumor; c) culturing said T cells in a first culture media, said media comprising one or more superantigens so as to specifically stimulate a subset of Vβ-expressing T cells; d) culturing said T cells in a second culture media, said media comprising human interleukin 2 so as to cause cell proliferation, thereby increasing the number of cells in said culture; and e) re-introducing at least a portion of said T cells into said patient so as to induce an in vivo therapeutic, tumoricidal reaction. In one embodiment, the method further comprises the step of administering human interleukin 2 to said patient in vivo after re-introducing said cells in step (e).

For culturing, the superantigen may comprise the enterotoxin SEB at concentrations above approximately 0.010 μg/ml. Preferably, the first culture media contains SEB at a concentration of approximately 2 μg/ml or greater and the second culture media contains human interleukin 2 at concentrations above 2 international units per milliliter.

DESCRIPTION OF THE FIGURES

FIG. 2 shows a comparison of the primary sequences of the staphylococcal enterotoxins and their relatives.

DESCRIPTION OF THE INVENTION

Figure 1:
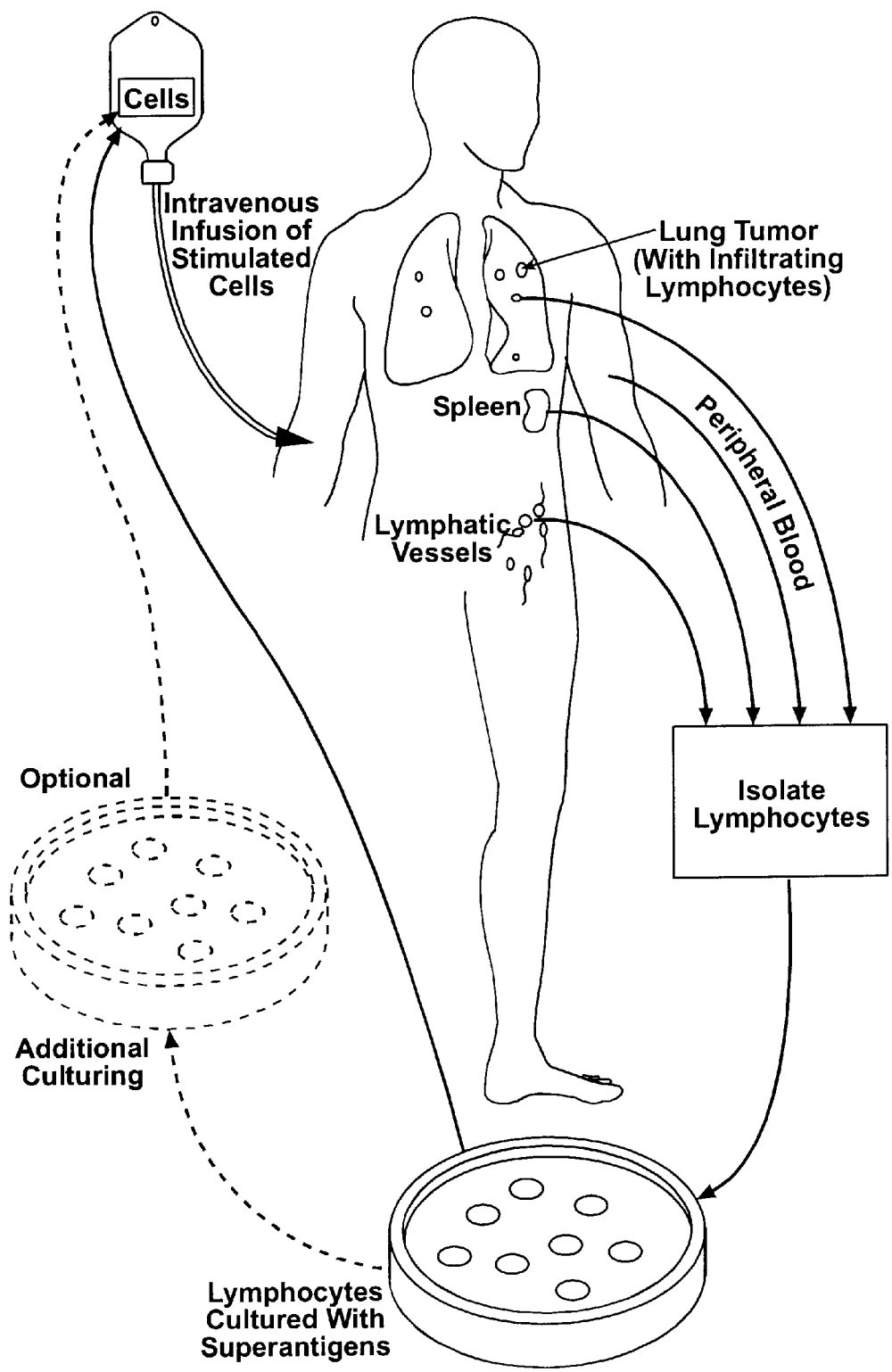
FIG. 1 schematically shows the therapeutic approach of the present invention.

The invention generally relates to the treatment of cancer, and more specifically, the treatment of solid tumors, including their metastases, without radiation, surgery or standard chemotherapeutic agents. In one embodiment, the invention involves a method wherein host cells are removed and stimulated outside the body, i.e., ex vivo, with stimulating antigens (see FIG. 1). These stimulated cells are later reintroduced into the same host to mediate anticancer effects. When administered to subjects having tumors, the stimulated cells induce a tumoricidal reaction resulting in tumor regression.

It should be understood that the term, "tumoricidal reaction," as used herein, means that the tumor cells are killed, and is not meant to be limited to any particular method by which tumor cells are killed. For example, it may be that the tumor cells are killed directly (e.g., cell-cell interaction) or indirectly (e.g., release of cytokines like interferon) by the reinfused, stimulated cells. On the other hand, the stimulated cells, while not secreting cytokines themselves, may cause changes in paracrine growth signals.

With respect to the latter, it is known that metastatic cells receive and process negative paracrine growth signals, e.g., from molecules in the transforming growth factory-β family of cytokines. In conjunction with positive growth factors, the negative growth factors could determine metastatic cell growth at particular sites.

In one embodiment, the stimulating antigens are selected from among the staphylococcal enterotoxins. The staphylococcal enterotoxins and toxic shock syndrome toxin, have extraordinary properties as T cell antigens. Like other antigens, T cell stimulation by these toxins is believed to be dependent upon presentation by Major Histocompatability Complex (MHC) molecules. In contrast to conventional antigens, however, they apparently do not require presentation by a "self" MHC molecule; allogeneic antigen-presenting cells are equally effective. It is thought that the essential requirement is that cells presenting the toxins express MHC class II molecules, as these molecules specifically bind the toxins.

The staphylococcal toxins are believed not to be "processed" within antigen-presenting cells to oligopeptides that are displayed to T cells within the class II antigen-binding groove. Instead, it is postulated that the intact protein binds outside the groove and interacts directly with T cell receptors for antigen. Most importantly, there is evidence that the staphylococcal toxins bind to a site on the Vβ segment of the T cell receptor heterodimer that is distinct from the complex site for binding of self MHC and foreign peptide antigen. Because the toxins do not bind to a site constituted by the full array of Vβ, Dβ, Jβ, Vα, and Jα gene products, the frequency of T cells responding to these molecules exceeds that of conventional peptide antigens by several orders of magnitude. Hence their name, "superantigens."

Antitumor effects may reside in specific subsets of T cells with Vβ phenotypes which may or may not have had prior exposure to tumor. These clones may have been deleted in the course of life by an antigenic stimulus or they may be genetically absent. Superantigens have the capacity to activate selective Vβ subsets and expand their numbers significantly, alone or together with IL-2. This stimulation may be carried out ex vivo with T cells presensitized to the tumor in vitro or in vivo, and simultaneously or sequentially incubated with various superantigens. These stimulated T cell subsets can be collected selectively (e.g., with a fluorescent or magnetic cell sorter), expanded in numbers with agents such as IL-2 and reinfused into the host, producing a tumoricidal reaction. It is possible that not one but several Vβ clones expanded by superantigens may work additively or synergistically to enhance the antitumor effect.

It is possible that certain Vβ subsets may exert suppressor effects on the tumoricidal activity. Optimal antitumor effects might be obtained after expansion of the Vβ clones having antitumor activity and depletion of the Vβ clones having suppressor activity, followed by reinfusion of the cells into the host. Selection of the Vβ clone to be expanded can be obtained by analysis of Vβ profiles of tumor infiltrating lymphocytes as well as from lymph node and peripheral blood Vβ T cell profiles. Cytotoxic or tumoricidal activity in vitro of a given Vβ subset or enrichment of a Vβ subset at a specific tumor location following parenteral administration in vivo might also assist in identification of the Vβ subsets with antitumor activity.

Tumor specific Vβ subsets may show different cytokine secreting profiles depending on the superantigen employed for stimulation. A preponderance of interferon γ production by tumor specific T cells stimulated by a given superantigen may render these cells more potent tumoricidal agents, compared to another Vβ subset stimulated by a different superantigen.

It is not intended that the invention be limited by the origin or nature of the host cells. Preferably, they are hematopoietic cells, such as immune cells (e.g., tumor infiltrating lymphocytes) or cells capable of developing into immune cells. While they may be isolated from a variety of sources, such as bone marrow (e.g., from femurs by aspiration), spleen or peripheral blood (e.g., collected with heparin and separated by Ficoll/hypaque gradient), as well as from the tumor (e.g., tumor-infiltrating lymphocytes). It is preferred that they are obtained from the lymph nodes. While they may be obtained from normal, disease-free donors, it is also preferred that they be obtained from tumor-bearing hosts.

TUMOR-DRAINING LYMPH NODES

It has been known that tumor draining lymph nodes contain T cells specifically sensitized to the growing tumor, although such cells are insufficient to mediate an antitumor response. These cells, termed "pre-effector" cells, can differentiate into functional immune cells upon further in vitro stimulation. Several culture techniques have been developed for successful generation of antitumor effector cells from tumor draining lymph nodes. S. Shu et al., J. Immun., 139:295–304 (1987). B. Ward et al., J. Immun., 141:1047–1053 (1988). T. Chou et al., J. Immun., 141:1775–1781 (1988). Initially, irradiated tumor cells were used to drive the maturation of draining lymph node cells, and, more recently, anti-CD3 monoclonal antibody and IL-2 were used. H. Yoshizawa et al., J. Immun., 147:729–737 (1991). However, the results reveal less than complete killing. While not limited by an understanding of the mechanism, this may be due to polyclonal stimulation with the particular stimulating agents used, i.e., generation of a significant proportion of immune cells with irrelevant specificity.

SUPERANTIGENS AS STIMULATING AGENTS

The approach of the present invention is to use more effective stimulating agents. Again, while not limited by an understanding of the mechanism, it is believed that so-called "superantigens" are capable of selectively activating subsets of T cells responsible for mediating the desired immune response.

Among the best studied superantigens are enterotoxins produced by *Staphylococcus aureus*. These superantigens are single chain proteins with molecular weights ranging from 22,000 to 38,000, and more particularly between 24,000 and 30,000. They are heat stable and resistant to trypsin digestion (the general properties of the enterotoxins are given in Table 1A and 1B). According to one aspect of the present invention, enterotoxins isolated from media which are supporting the growth of various *Staphylococcus aureus* organisms are used.

The enterotoxins of *Staphylococcus aureus* form a group of serologically distinct extracellular proteins, designated A, B, $C_1$, $C_2$, $C_3$, D, E and F. These proteins are recognized as the causative agents of Staphylococcal food poisoning. Enterotoxin F appears to be important in the pathogenesis of the Staphylococcal toxic shock syndrome.

It is not intended that the present invention be limited by the origin or nature of the particular enterotoxin. Indeed, synthetic polypeptides with substantial structural homology and with statistically significant sequence homology and similarity to Staphylococcal enterotoxins and Streptococcal pyrogenic exotoxins, including alignment of cysteine residues and similar hydropathy profiles, may also be effective stimulants ex vivo to induce a tumoricidal reaction when the stimulated cells are reinfused. In addition to enterotoxins, such peptides might be derived from, but are not limited to sequences in additional superantigens such as minor lymphocyte stimulating loci, mycoplasma and mycobacterial, Yersinia and Streptococcal Protein M antigens, heat shock proteins, stress peptides, and mammary tumor viruses.

The protein sequences and immunological cross-reactivity of the enterotoxins reveal that they can be divided into two related groups. The Staphylococcal enterotoxins A, E and D (SEA, SEE and SED) constitute one group, and Staphylococcal enterotoxins B and C (SEB, SEC) and Streptococcal pyrogenic exotoxin A (SPEA) make up the second group. Amino acid sequences show that SEA and SEE are almost identical and that SEB, SEC and SPEA share regions of similar sequence (amino acid sequence similarities and congruences are given in Tables 2–4). SED is moderately related to both groups although it is more similar to the SEA group. There is a striking amino acid similarity among enterotoxins A, B, C, D and E in the region immediately downstream from cysteine located at residue 106 in SEA. A second region at residue 147 also shows a highly conserved sequence.

TABLE 1A

Some Properties Of The Enterotoxins

| | Enterotoxin | | | |
|---|---|---|---|---|
| | $A^a$ | $B^b$ | $C_1^c$ | $C_2^d$ |
| Emetic dose ($ED_{50}$) (μg/monkey) | 5 | 5 | 5 | 5–10 |
| Nitrogen content (%) | 16.5 | 16.1 | 16.2 | 16.0 |
| Sedimentation coefficient ($S_{20,w}$) (S) | 3.04 | 2.78 | 3.00 | 2.90 |
| Diffusion coefficient ($D_{20,w}$) ($\times 10^{-7}$ cm$^2$ sec$^{-1}$) | 7.94 | 8.22 | 8.10 | 8.10 |
| Reduced viscosity (ml/g) | 4.07 | 3.81 | 3.4 | 3.7 |
| Molecular weight | 34,700 | 30,000 | 34,100 | 34,000 |
| Partial specific volume | 0.726 | 0.726 | 0.728 | 0.725 |
| Isoelectric point | 6.8 | 8.6 | 8.6 | 7.0 |
| Maximum absorption (mμ) | 277 | 277 | 277 | 277 |
| Extinction ($E_{1\,cm}^{1\%}$) | 14.3 | 14.4 | 12.1 | 12.1 |

[a] F. S. Thadhani et al., Biochem., 5:3281 (1966).
[b] M. S. Bergdoll et al, J. Bacteriol., 90:1481 (1965).
[c] C. R. Borja and M. S. Bergdoll, Biochem., 6:1467 (1967).
[d] R. M. Avena and M. S. Bergdoll, Biochem. 6:1474 (1967).

TABLE 1B

Physicochemical Properties Of Staphylococcal Enterotoxins*

| Property | Enterotoxin | | | | | |
|---|---|---|---|---|---|---|
| | A[a] | B[b] | $C_1$[c] | $C_2$[d] | D[e] | E[f] |
| Emetic dose for monkey (μg) | 5 | 5 | 5 | 5–10 | — | — |
| Sedimentation coefficient ($S_{20,w}$) | 3.03 | 2.89 | 3.0 | 2.9 | — | 2.6 |
| Molecular weight | 27,800 | 28,366[g] | 26,000 | 34,100 | 27,300 | 29,600 |
| Isoelectric point | 7.26 | 8.6 | 8.6 | 7.0 | 7.4 | 7.0 |
| C-terminal residue | Serine | Lysine | Glycine | Glycine | Lysine | Threonine |
| N-terminal residue | Alanine | Glutamic acid | Glutamic acid | Glutamic acid | Serine | — |

[a]E. J. Schantz et al, Biochem., 11:360 (1972).
[b]E. J. Schantz et al, Biochem. 4:1011 (1965).
[c]C. R. Borja and M. S. Bergdoll, Biochem., 6:1467 (1967).
[d]R. M. Avena and M. S. Bergdoll, Biochem. 6:1474 (1967).
[e]P. C. Chang and M. S. Bergdoll, Biochem., 18:1937 (1979).
[f]C. R. Borja et al, J. Biol. Chem., 247:2456 (1972).
[g]Data Section in Atlas Protein Sequence Structure 5:D227, (M. Dayhoff, ed.), National Biomedical Research Foundation, Washington D.C. (1972) (determined from the amino acid sequence of I. Y. Huang and M. S. Bergdoll, J. Biol. Chem., 245:3493 (1970)).
*Modified from M. S. Bergdoll et al in Recent Advances in Staphylococcal Research, (W. W. Yotis, ed.), Ann. N.Y. Acad. Sci., 236:307–316.

These regions are contained on the peptide fragment of SEC, and are known to contain the active sites for emesis and diarrhea. The mitogenic region resides in the C terminal tryptic fragment of SEC, implying that other regions of sequence similarity exist.

Figure 2:
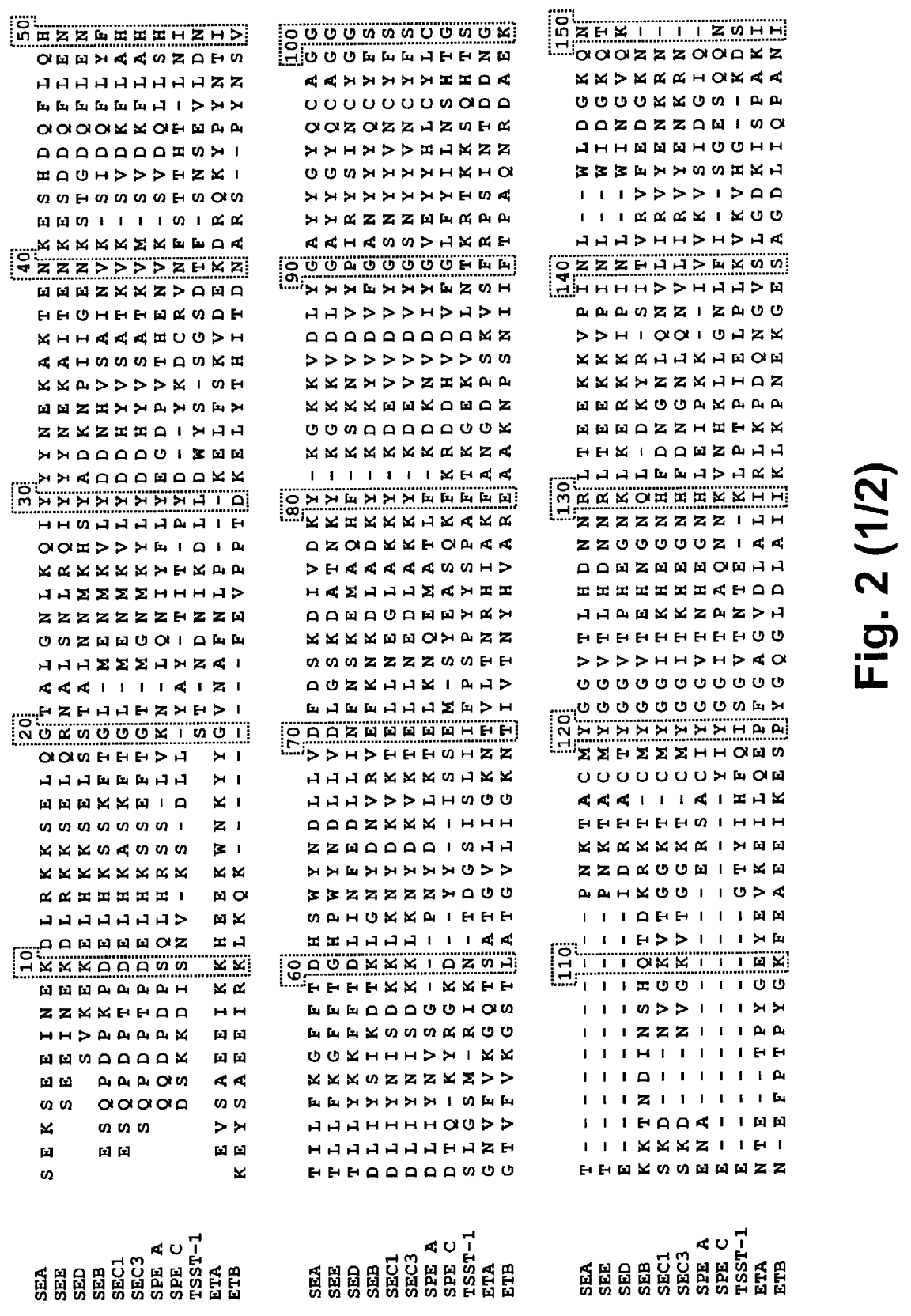
Figure 2:
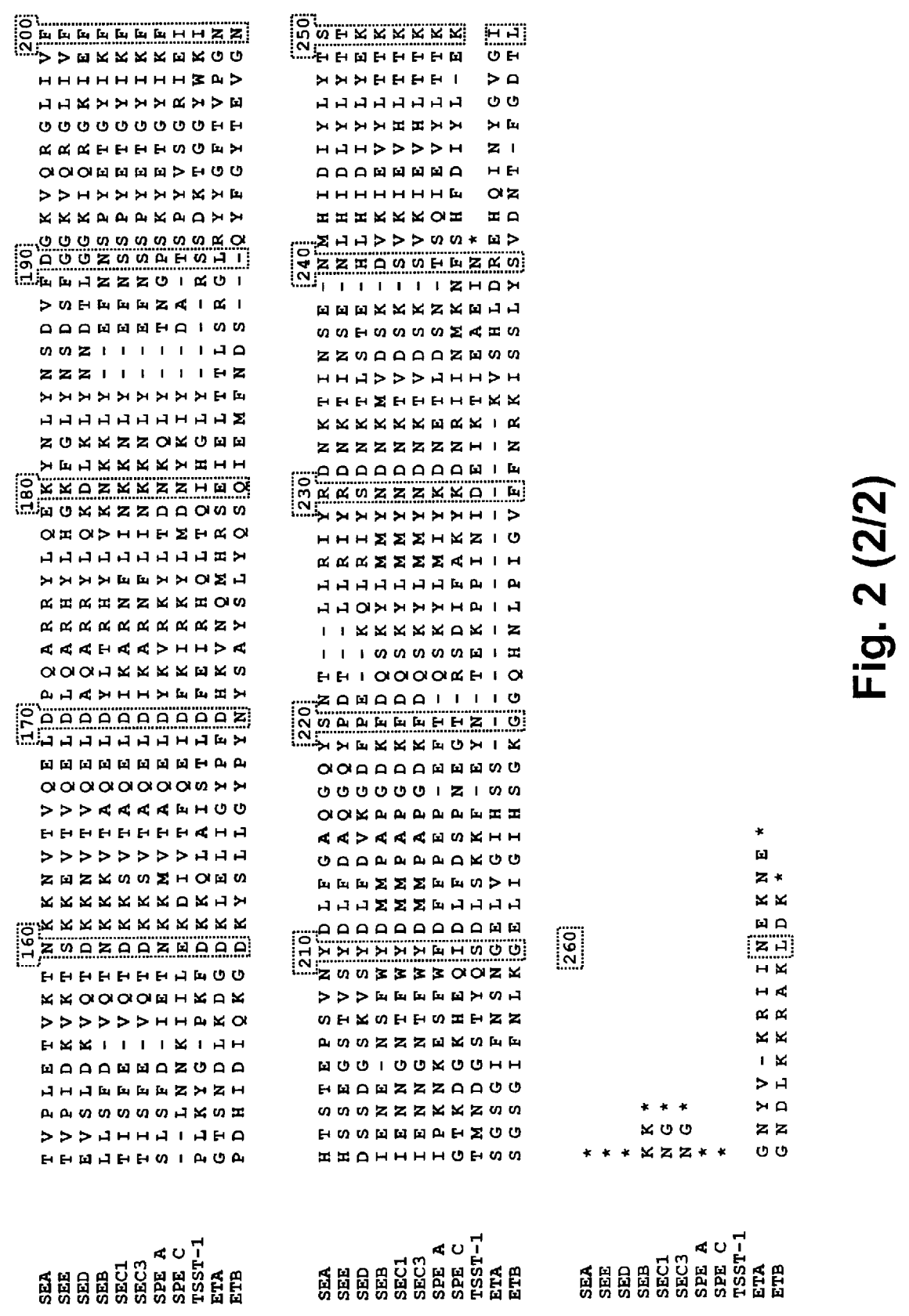

Comparison of the primary sequences of the staphylococcal enterotoxins and their relatives is shown in FIG. 2. The complete primary amino acid sequences of the staphylococcal enterotoxins and related proteins are shown aligned, with the exception of the sequences of the exfoliating toxins, which are shown aligned with each other, but not with the remaining toxins. The exfoliating toxins have properties related to those of the others.

TABLE 2*

Sequence Similarities Among The Pyrogenic Toxins And Enterotoxins

| Toxin | Sequence | |
|---|---|---|
| | 106        119 | 147        163 |
| SEA | CMYGGVTLHDNNRL | KKNVTVQELDLQARRYL |
| SEB | CMYGGVTEHHGNOL | KKKVTAQELDYLTRHYL |
| SEC1 | CMYGGITKHEGNHF | KKSVTAQELDIKARNFL |
| SED | CTYGGVTPHEGNKL | KKNVTVQELDAQARRYL |
| SEE | CMYGGVTLHDNNRL | KKEVTVQELDLQARHYL |
| SPEA | CIYGGVTNHEGNHL | KKMVTAQELDYKVRKYL |

TABLE 2*-continued

Sequence Similarities Among The Pyrogenic Toxins And Enterotoxins

| Toxin | Sequence | |
|---|---|---|
| Consensus | CMYGGVTLHEGNHL | KKNVTAQELD$\overset{L}{\text{T}}$QAR$\overset{R}{\text{H}}$YL |
| TSST-1 | IHFQISGVTNTEKL | KKQLAISTLDFEIRHQL |

*J. J. Iandolo, Ann. Rev. Microbiol., 43:375(1989).

TABLE 3

Amino Acid Composition Of The Enterotoxins (g/100 g Protein)

| Amino Acid | Enterotoxin | | | | |
|---|---|---|---|---|---|
| | A* | B† | $C_1$‡ | $C_2$‡ | E§ |
| Lysine | 11.26 | 14.85 | 14.43 | 13.99 | 10.83 |
| Histidine | 3.16 | 2.34 | 2.91 | 2.87 | 3.04 |
| Arginine | 4.02 | 2.69 | 1.71 | 1.75 | 4.50 |
| Aspartic acid | 15.53 | 18.13 | 17.85 | 18.38 | 15.10 |
| Threonine | 5.96 | 4.50 | 5.31 | 5.80 | 6.36 |
| Serine | 2.99 | 4.05 | 4.58 | 4.81 | 4.72 |
| Glutamic acid | 12.36 | 9.45 | 8.95 | 8.93 | 12.15 |
| Proline | 1.35 | 2.11 | 2.16 | 2.23 | 1.93 |
| Glycine | 2.96 | 1.78 | 2.99 | 2.90 | 4.10 |
| Alanine | 1.94 | 1.32 | 1.85 | 1.61 | 2.38 |
| Half-cysteine | 0.66 | 0.68 | 0.79 | 0.74 | 0.81 |
| Valine | 4.93 | 5.66 | 6.50 | 5.87 | 4.36 |
| Methionine | 0.96 | 3.52 | 3.20 | 3.60 | 0.45 |
| Isoleucine | 4.11 | 3.53 | 4.09 | 4.02 | 4.30 |
| Leucine | 9.78 | 6.86 | 6.54 | 6.13 | 10.08 |
| Tyrosine | 10.63 | 11.50 | 9.80 | 10.27 | 9.79 |
| Phenylalanine | 4.31 | 6.23 | 5.35 | 5.25 | 4.47 |
| Tryptophan | 1.46 | 0.95 | 0.99 | 0.84 | 1.51 |
| Amide $NH_3$ | 1.80 | 1.66 | 1.71 | 1.62 | 1.66 |
| TOTAL | 98.37 | 100.15 | 100.00 | 99.99 | 100.88 |

*Schantz et al., 1972.
†M. S. Bergdoll et al, Arch Biochem Biophys, 112:104 (1965).
‡I. Y. Huang et al, Biochem., 6:1480 (1967).
§Borja et al., 1972.
¶M. S. Bergdoll et al., Agric. Food Chem., 22:9 (1974).

TABLE 4†

Amino Acid Compositions Of TSST-1a And 1b[a]

| Amino acid | Amino acid composition | | |
|---|---|---|---|
| | TSST-1a residues per mole[b] | TSST-1b residues per mole[b] | Clone[b] |
| Aspartic acid | 26 | 27 | 25 |
| Threonine | 21 | 20 | 19 |
| Serine | 20 | 20 | 21 |
| Glutamic acid | 20 | 20 | 17 |
| Proline | 10 | 8 | 10 |
| Glycine | 13 | 14 | 11 |
| Alanine | 4 | 5 | 3 |
| Half-cysteine | 0 | 0 | 0 |
| Valine | 5 | 5 | 5 |
| Methionine | 0 | 0 | 2 |
| Isoleucine | 15 | 15 | 17 |
| Leucine | 14 | 16 | 15 |
| Tyrosine | 10 | 8 | 9 |
| Phenylalanine | 7 | 7 | 7 |
| Histidine | 5 | 5 | 5 |
| Lysine | 23 | 24 | 21 |

TABLE 4[†]-continued

Amino Acid Compositions Of TSST-1a And 1b[a]

Amino acid composition

| Amino acid | TSST-1a residues per mole[b] | TSST-1b residues per mole[b] | Clone[b] |
|---|---|---|---|
| Tryptophan | ND[d] | ND[d] | 3 |
| Arginine | 4 | 5 | 4 |
| TOTAL | 197 | 199 | 194 |

[†]D. A. Blomster-Hautamaa and P. M. Schlievert, Meth. Enzym., 165:37 (1988).
[a]Isolated from strain MN8, as compared to the inferred amino acid composition of the TSST-1 structural gene.
[b]Residues per mole values are based on a molecular weight of 22,000.
[c]Residues per mole inferred from the DNA sequence of the TSST-1 structural gene. Blomster-Hautamaa and colleagues.
[d]ND. Not determined.

The toxins shown in FIG. 2 are as follows: SEA to SEE, *Staphylococcus aureus* enterotoxins A to E; SPE A and C, *Streptococcus pyogenes* toxins A and C; TSST1, *Staphylococcus aureus* toxic shock—associated toxin; ETA and ETB, *Staphylococcus aureus* exfoliating toxins A and B. Single letter abbreviations for the amino acid residues are: A, Ala; C, Cys; D, Asp; E, Glu; F, Phe; G, Gly; H, His; I Ile; K, Lys; L, Leu; M, Met; N, Asn; P, Pro; Q, Gln; R, Arg; S, Ser; T, Thr; V, Val; W, Trp; and Y, Tyr.

It should be noted that the two Streptococcal toxins SPEA and C are about as similar to each of the Staphylococcal groups as they are to each other. Exfoliative toxins (ETA, ETB) are of similar size to SEB and SEA with similar modes of action. They share several points of sequence similarity to the Staphylococcal enterotoxins. Overall there are several stretches at which similarities are apparent throughout the total group comprised of Staphylococcal enterotoxins, Streptococcal pyrogenic exotoxins and Staphylococcal exfoliative toxins.

The recognition that the biologically active regions of the enterotoxins and SPEA were substantially structurally homologous enables one to predict synthetic polypeptide compounds which will exhibit similar tumoricidal effects. Table 6 illustrates the amino acid sequence homology of mature SPEA and *Staphylococcus aureus* enterotoxin B. The top sequence is the SPEA-derived amino acid sequence. The amino acid sequence of enterotoxin B is on the bottom. Sequences are numbered from the amino acid terminus, with amino acids represented by standard one character designations (see Table 5). Identities are indicated by: and gaps in the sequences introduced by the alignment algorithm are represented by dashed lines. [See L. P. Johnson et al., Mol. Gen. Genet., 203:354–356 (1986).]

One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant. W. R. Pearson and D. J. Lipman, Proc. Natl. Acad. Sci. (USA), 85:2444–2448 (1988); and D. J. Lipman and W. R. Pearson, Science, 227:1435–1441 (1985).

In the present invention, synthetic polypeptides useful in tumoricidal therapy and in blocking or destroying autoreactive T and B lymphocyte populations are characterized by substantial structural homology to enterotoxin A, enterotoxin B and streptococcal pyrogenic exotoxins with statistically significant sequence homology and similarity (Z value of Lipman and Pearson algorithm in Monte Carlo analysis exceeding 6) to include alignment of cysteine residues and similar hydropathy profiles.

TOXICITY OF SUPERANTIGENS

Previous approaches utilizing superantigens in cancer therapy have involved systemic exposure to these agents. Such early approaches include both plasma perfusion over a solid support matrix containing superantigens [D. S. Terman et al., New Eng. J. Med., 305:1195 (1981)] as well as direct injection of superantigens into a tumor-bearing host. D. S. Terman, patent application Ser. No. PCT/US91/00342 (1990); K. A. Newell et al., Proc. Nat. Acad. Sci (USA), 88:1074 (1991).

It is believed that all enterotoxins are capable of inducing fever and shock when given systemically (e.g., intravenously). When administered in this manner, they are presumed to finction by affecting emetic receptors in the abdominal viscera which stimulate the emetic and diarrheal response. They are also believed to induce interferon, tumor necrosis factor, and interleukins 1 and 2.

Unfortunately, the increased effectiveness of higher doses of systemically introduced superantigens is correlated with higher toxicity. In this regard, direct administration of increasingly effective, anti-cancer doses in animals has been followed by shock and death within 12–24 hours.

TABLE 5

| Amino Acid | One-letter Symbol |
|---|---|
| Alanine | A |
| Arginine | R |
| Asparagine | N |
| Aspartic acid | D |
| Cysteine | C |
| Glutamine | Q |
| Glutamic acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

TABLE 6

```
            10         20         30         40         50
STR-PKPSQLQRSNLVKTFKIYIFFMRVTL-----VTHENVKSVDQLLSHDLIYNVS--
  : :::    :  :   : :           :     ::::        :::: :
ESQPDPKPDELHKSS--K-FTGLMENMKV-LYNNDHVSAINVKSINEFF--DLIYLYSIK
       10         20         30         40         50

60         70         80         90
----GPNYDKLKTELKNQEMATLFKDKNVDIYGVEYYHLCYLC---------ENAERSAC
    : :::     :  ::     :    ::: ::   :  ::  ::        ::    : :
DTKLG-NYDNVRVEFKNKDLADKYKDKYVDVFGANYYQ-CYFSKKTNNIDSHENTKRKTC
      60         70         80         90        100        110

100         110            120         130        140        150
LYGGVTNHEGNHLEIPKK----IVVKVSIDGIQSLSFDIEQIKNGNCSRIS-YTVRKYLT
 : ::::  : :    : :           :        : : :   ::   ::::           :     : ::
MYGGVTEHGNNQLD---KYYRSITVRVFEDGKNLLSFDVQTNKKKVTAEQLDYLTRHYLV
       120           130         140        150        160

160        170        180       190        200
DNKQLYTNGPSKYETGYIKFIPKNKESFWFDFFPEPE--FTQSKYLMIYKDNETLDSNTS
 :: ::      : ::::::::::  :  :::  :   : :     : ::::::: :          ::
KNKKLYEFNNSPYETGYIKFIE-NENSFWYDMMPAPGNKFDQSKYLMMYNNDKMVDSKDV
 170        180        190         200        210        220

220
QIEVYLTTK
 ::::::::
KIEVYLTTKKK
  230
```

The present invention contemplates avoiding the undesirable effects, but nonetheless harnessing the valuable characteristics of superantigens. Preferably, there is no significant systemic exposure to superantigens using the ex vivo stimulation approach of the present invention.

It should be noted that the ex vivo approach also allows for the presence of minor impurities in the preparation that would be unacceptable in preparations for direct administration. While these impurities might be toxic (or even lethal) in vivo, they can simply be washed away along with the superantigen itself following ex vivo culture.

In sum, the criteria for superantigens, and in particular, superantigen purity are: 1) mitogenic activity in a tritiated thymidine proliferation assay, 2) stimulation of interferon release, 3) Vβ cell reactivity, 4) amino acid profile (see above), 5) HPLC and PAGE (21–28,000 MW); 6) negative in the limulus amebocyte lysate (LAL) test for endotoxin; 7) negative in a hemolytic assay for the presence of alpha-hemolysin.

EX VIVO STIMULATION

As noted above, a number of cell types can be used. When cells from lymph nodes are used, all types of lymph nodes are contemplated (inguinal, mesenteric, superficial distal auxiliary, etc.). For ex vivo stimulation, they are removed aseptically and single cell suspensions are prepared by teasing under sterile conditions. Cell preparations then may be filtered (e.g., through a layer of nylon mesh), centrifuged and subjected to a gentle lysing procedure, if necessary.

Tumor-draining lymph node cells may be stimulated in vitro using a number of protocols. For example, a sufficiently large number of lymph node cells (i.e., a number adequate to show a tumoricidal reaction upon reinfusion) are exposed to superantigens (e.g., SEA, SEB, etc.) and diluted in synthetic culture media (e.g., RPMI 1640 with typical supplements) for the appropriate period of time (e.g., two days). Any number of standard culture techniques can be employed (e.g., 24-well plates in an incubator at 37° C. in a 5% $CO_2$ atmosphere).

Following the incubation, the stimulated cells are harvested and washed with synthetic media containing no superantigens. At this point, the cells may be cultured further with other agents if desired (e.g., IL-2). In any event, the cells are counted to determine the degree of proliferation and resuspended in appropriate media for therapy.

The stimulated cells may be reintroduced to the host by a number of approaches. Preferably, they are injected intravenously. Optionally, the host may be treated with agents to promote the in vivo function and survival of the stimulated cells (e.g., IL-2).

Of course, the stimulated cells may be reintroduced in a variety of pharmaceutical formulations. These may contain such normally employed additives as binders, fillers, carriers, preservatives, stabilizing agents, emulsifiers, and buffers. Suitable diluents and excipients are, for example, water, saline, and dextrose.

ALTERNATE EMBODIMENTS

Tumor resensitized lymphocytes may become anergized in the course of tumor growth in vivo and become refractory to activation or expansion by the superantigens with T cell Vβ specificity. Various cytokines may partially reverse T memory cell anergy, namely, IL-2, IL-4, or IL-1 plus IL-6. These cytokines may promote T cell proliferation and may represent an essential "second signal" typically provided by antigen presenting cells. Hence, responsiveness of tumor sensitized lymphocytes may be restored by co-culturing with various cytokines and mitogens such as anti-CD3 antibody or conconavalin A.

While the preferred embodiment involves culturing ex vivo, other approaches are also contemplated. In one embodiment, the present invention contemplates transfecting with superantigen genes into tumor cells to provide powerful augmenting signals to T cell stimulation. In another embodiment, dual transfection with superantigens and molecules such as B7 is contemplated. Moreover, various cytokines and antibodies which are known to enhance T cell proliferation and secretion such as interleukin 1, interleukin 2, interleukin 4, interleukin 6, anti-CD3 or anti-CD2 may be employed simultaneously or sequentially with enterotoxins in vivo or in vitro to augment antitumor effects of the enterotoxins.

Substances which increase the number of antigen-presenting cells, as well as substances which induce up-regulation of class II molecules on antigen-presenting cells or T cells, such as Y interferon, ICAM molecules and the like, used in vitro or in vivo could create additional binding sites for superantigen presentation to the T lymphocyte population and augment T lymphocyte proliferative and secretory function as well as anti-tumor effects.

Differences of antitumor reactivities between SEA and SEB stimulated cells probably represent distinct T cell subsets with Vβ phenotypes responding to these two superantigens. If a population of T cells with specific Vβ phenotype appears to mediate the antitumor effects, selective depletion of the ineffective subsets and expansion of the fraction of effective subset(s) can be carried out with immunomagnetic beads or monoclonal antibodies. Alternatively, if a major tumor-killing Vβ subtype T cell population is found to be deleted, that population may be reconstituted with T cells transfected with the specific Vβ genes by various transfection techniques now in use in the field. Such a reconstituted T cell clone can be stimulated with appropriate tumor antigen in vitro or in vivo to create a presensitized T cell population and then with enterotoxin, plus antigen presenting cell APC stimulus. After expansion in IL-2, this reconstituted T cell clone would be expected to restore T cell function and antitumor activity to the deleted clone.

Finally, various superantigens may be employed sequentially to up-regulate the activity of one another. For example, SEA, which is known to be a powerful cytokine inducer, may be used in vitro or in vivo to up-regulate class II molecules before the use of SEB or SEC, which are potent T cell stimulants. The up-regulated class II binding sites created by SEA would be occupied by SEB, providing significantly increased antigenic presentation to the T cell Vβ repertoire.

In a canine model using the Protein A collodion charcoal (PACC) system described in a series of patent applications (for example, U.S. patent application Ser. No. 331,095, the forerunner of the present invention), therapeutic success was transferred to humans in protocols in which objective tumor regressions were obtained in four of the first five consecutive patients treated. Thus, the data given herein also is expected to be predictive of success when the compositions are applied to humans.

Enterotoxin Genes: Genetically Engineered Tumor Cells, Accessory Cells, and Peptides The genes for the enterotoxins and streptococcal pyrogenic exotoxins have been cloned. With their known mimicry of the Mls locus and their affinity for T cell Vβ receptors, it would be logical to assume that transfection of the enterotoxin gene into tumor cells bearing appropriate HLA-DQ or DR or DP would result in production of a tumor cell bearing the minor lymphocyte stimulating locus capable of ligating MHC class II molecules with T lymphocytes, therefore stimulating potent T cell proliferation and associated antitumor immunity. Experiments are being designed and implemented to test this hypothesis. The rabbit VX-2 carcinoma cells have been established in tissue culture. The gene for enterotoxins A and B have been isolated and have been made available for these studies by Dr. Marcia Betley and Dr. Saleem Khann, respectively. Plans for transfection of rabbit VX-2 carcinoma cells with both genes have been made with Dr. Susan Faas and Dr. John McIntyre of Tektagen, Malverne, Pa. The transfected cells will then be injected into rabbits bearing the VX-2 carcinoma with appropriate controls consisting of non-transfected rabbit VX-2 carcinoma cells and VX-2 cells transfected with an irrelevant microbial genes. Anti-tumor effects will be assessed in this system.

Alternatively, the toxin gene transfected tumor cells could be used for in vitro stimulation of host immunocytes prior to or coordinate with the addition of interleukin 2 to produce an enriched population of tumor specific T cells which could then be reinfused into a tumor bearing host and would be expected to exert tumor killing effects.

The enterotoxin gene could be used to transfect various accessory cells resulting in enterotoxin expression on the cell surface which may then induce more potent stimulation and proliferation of tumoricidal T lymphocytes. The cotransfection of these accessory cells with adhesion molecules and MHC molecules might further augment the mitogenic activity of T lymphocytes induced by these accessory cells.

Mutant genes of the toxins could be used to transfect various bacteria such as *E. coli* resulting in the production of toxin peptides retaining antitumor activity. Such superantigen peptides might have sequences homologous with various naturally occurring viruses such as mammary tumor virus, endogenous proteins such as heat shock proteins, stress proteins and minor lymphocyte stimulating loci, naturally occurring bacteria such as mycoplasma and mycobacterial species. Amino acid sequences in the native toxin molecules associated with toxicity such as emesis, excessive cytokine induction or humoral antibody production would be deleted. For example, histadine residues of SEB may account for emetic responses of the SEB molecule since carboxymethylation of the SEB molecule selectively blocks histadine moieties resulting in a reduction of the emetic response. Additional mutant genes might be employed to produce peptides which bind selectively to T lymphocytes or class II molecules without stimulating mitogenesis, cytokine or antibody production. As such, these genetically engineered molecules might be used to block or eliminate autoimmune responses induced by proliferation of clones of immunocytes reactive to self constituents such as basic myelin protein in multiple sclerosis or synovial constituents in rheumatoid arthritis.

Moreover, enterotoxin genes would be fused with genes from other bioactive compounds such as cell poisons to produce molecules with capacity to destroy a selective cell population. Such fusion peptides might include enterotoxin sequences fused, for example, with peptides of pseudomonas toxin, diphtheria toxin sequences or antibodies yielding complexes retaining the major structural, biologic features of the native proteins.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); mM (millimolar); N (Normal); mol (moles); mmol (millimoles); μmol (micromoles); nmol (nanomoles); g (grams); mg (milligrams); μg (micrograms); L (liters); ml (milliliters); μl (microliters); cm (centimeters); mm (millimeters); μm (micrometers); um (nanometers); ° C. (degrees Centigrade); mAb (monoclonal antibody); MW (molecular weight); U (units); d(days).

EXAMPLE 1

Production And Isolation Of Enterotoxins

This example describes the preparation of enterotoxins. The preparation of enterotoxin has been described in detail, previously; specifically, in patent application, Ser. No. 07/891,718, filed Jun. 1, 1992, the entire contents of which are hereby incorporated by reference.

This example describes two purification approaches for Enterotoxins A and $C_2$.

Approach 1: A 10 ml culture of *Staphylococcus aureus* 11N-165 (SEA), *Staphylococcus aureus* 361 (Source: Dr. John landolo, Kansas State University, Manhattan, Kans.) ($SEC_2$) is grown overnight at 37° C. The removal of enterotoxin from the supernatant is carried out using QAE-Sephadex. The toxin is then eluted batchwise from the ion exchanger and recovered by filtration on a sintered glass funnel. The eluates are concentrated by ultrafiltration. The toxin is then passed through a Sephadex-G-100 column. Two peaks absorbing at 280 mm are eluted, with the latter containing the enterotoxin. The eluted toxin is concentrated and rerun on Sephadex-G-100. The overall recovery is about 30% for $SEC_2$ and 40 to 50% for SEA. Both toxins appear homogeneous by sodium dodecylsulfate polyacrylamide gel electrophoresis (SDS-PAGE).

Approach 2: Staphlococcus aureus Strain FRI-722 is grown in a 3% enzyme-hydrolyzed casein and 7% yeast extract at pH 6.6 at a temperature of 35–37° C. The mixture is gently agitated for 16–20 hours. The culture is filtered through a 0.2 micron filter and the filtrate pH is adjusted to 5.6. The filtrate is diluted 1:5 to 1:10 with deionized water, incubated with a cation exchange resin and stirred for 1 h. The resin is collected and the bound protein is eluted with high ionic strength buffer. The eluate is concentrated and dialyzed then reincubated with a second cation exchange resin. The SEA is eluted with a low ionic strength to high ionic strength buffer gradient. The fraction containing SEA is concentrated, dialyzed and loaded onto a gel filtration system. The fraction containing SEA is concentrated and dialyzed against PBS pH 7.2. The final solution is filter-sterilized and frozen. Total protein is determined spectrophotometrically at 280/260 nm. A 5 μg/ml solution is tested in gel diffusion against a known antisera to SEA and 1 μg/ml is tested in PAGE and endotoxin in the Sigma-E-Toxate LAL assay.

EXAMPLE 2

Production And Isolation Of Enterotoxins

This example describes a purification approach for Enterotoxins A and $C_7$ and D.

This approach utilizes fast protein liquid chromatography (FPLC) and high resolution chromatofocusing Mono P column. Enterotoxins in media are concentrated and passed over a Sephadex-G-75 column. The toxin containing fractions are pooled. For $C_1$ and D, the supernatants are passed over an AmberLite-CG-50 column, as described for SED, and the active fractions pooled. All three toxins are then placed in buffer for chromatofocusing and then separated using the MONO P column FPLC system. Since all of the toxins have isoelectric points in the range of 7 to 9, the polybuffer PBE-96 is used for elution. The purity of SEA, $SEC_1$ and SED is estimated to be 98, 95 and 80%, respectively. SEA elutes as two peaks at pH 8.8 and 8.6. $SEC_1$ also elutes as two peaks at pH 8.3 and 7.9, and SED elutes as three peaks at pH 8.6, 8.3 and 8.0.

Enterotoxins may also be produced in mutant strains of *Staphylococcus aureus* by expression of an enterotoxin producing gene in another bacteria or cell. Genetic material which appears to be in the chromosomal plasmid, or phage portion of the bacteria may be used for gene insertion procedures. Complete molecules or fragments with amino acid sequence homology to the parent enterotoxin may be produced with this technology. (Reviewed in Iandolo, J. J., Annu. Rev. Microbiol., 43:375 (1989). Moreover, mutagenic agents such as N-Nitroso compounds are capable of augmenting significantly the production of enterotoxins by some strains of Staphylococcus.

EXAMPLE 3

Production And Isolation Of Enterotoxins

This example describes a purification approach for Alpha Toxin.

*Staphylococcus aureus* Wood 46 strain (Source: Dr. Sidney Harshman, Vanderbilt University, Nashville, Tenn.) is used and cultured in yeast extract dialysate medium. With the glass-pore bead method undialyzed yeast may be used together with casein, glucose, thiamine and nicotinic acid. The organism is incubated in medium for 24 h at 370° C.

The culture supernatant is applied to a glass- pore bead column and adjusted to pH 6.8. A column of 5×20 cm is used for 3 liter batches and flow rates adjusted to 10–20 mumin. The column is washed with 0.01M $KHPO_4$ pH 6.8 and then the alpha toxin is eluted with 1.0M $KHPO_4$ pH 7.5. Fractions are tested for the presence of alpha hemolysin by a rapid hemolytic assay using rabbit erythrocytes as substrate.

EXAMPLE 4

Production And Isolation Of Enterotoxins

This example describes a purification approach for Streptococcal Pyrogenic Exotoxin (SPE).

Streptococcus NY-5 strain (Source: ATCC 12351) has been the most widely used for toxin production and studies. A list of various strains to produce toxins A, B, and C has been published. The Kalbach S84 type 3 strain (Source: Dr. Joseph E. Alouf, Institute Pasteur-Unite Associee, Paris, France) is cultured and the supernatant is concentrated and stirred in calcium phosphate gel. Fraction $S_1$ is precipitated with 80% saturated ammonium sulfate. The redissolved pellet is dialyzed and designated Fraction $S_2$. This fraction is precipitated with 50–80% ammonium sulfate, resuspended in phosphate buffered saline (Fraction $S_3$), and gel filtered on a Bio-Gel P-100 column. The fraction corresponding to the volume eluted between 160 and 240 ml is collected and concentrated by ultrafiltration to about 20 ml in an Amicon PM10 Membrane (Fraction $S_4$). Fraction S4 is then submitted to preparative isoelectric focusing (IEF) performed with a 100 ml column. The material which focuses at around pH 4.8 in a narrow peak is collected and dialyzed in an Amicon cell using PBS to eliminate ampholines and sucrose. The Fraction ($S_5$) constitutes purified pyrogenic exotoxin. Another electrophoretic form of SPE with a pI of 4.2 is often separated simultaneously with that of pI 4.8. Both forms show total cross reactivity against immune sera raised by rabbit immunization with fraction $S_3$.

The Fraction $S_5$ shows a single band by SDS-PAGE corresponding to a molecular weight of 28K. Bioassays for determination of activity include erythematosus skin test in rabbits or guinea pigs lymphocyte blast transformation. The toxin may also be detected by enzyme-linked immunoabsorbant assay (ELISA) or hemagglutination inhibition.

EXAMPLE 5

Production And Isolation Of Enterotoxins

This example describes a general purification approach for native enterotoxins.

Current methods for purification of all of the enterotoxins utilize ion exchange materials such as CG-50, carboxymethyl-cellulose and the Sephadexes (gel filtration). The preparation of the SEB used for these studies is as follows.

Staphylococcus aureus strain I10-275 is cultured in NZ-Amine A media supplemented with 10 g/liter of yeast extract for 18–20 hours in room air at 37° C. The flask is agitated at 300 RPM. The initial pH of the culture is 6.8 and the postincubation pH 8.0. The culture is filtered through a DC-10 Amicon filter (pore size 0.1 micron). The final filtrate is adjusted to pH 5.6. The filtrate is tested for the presence of SEB in radial immunodiffusion using known antisera to SEB. Eighteen to 20 liters of culture supernatant fluid are diluted with deionized, distilled $H_2O$ (1:5 to 1:10) and the pH adjusted to 5.6, CG-50 resin (Malinkrodt) (800 ml), preequilibrated to pH 5.6 in 0.03 M phosphate buffer, pH 6.2 (PB) is added and the mixture stirred for one hour. The resin is allowed to settle and the supernatant fluid is decanted. The resin is placed in a column and the toxin is eluted with 0.5 M PB, 0.5 M NaCl pH 6.2. The concentrated, dialyzed toxin is placed in a column (5 cm×75 cm) of CM-sepharose (pretreated with 0.005 M PB pH 5.6). The column is washed with the same buffer and the enterotoxin eluted by treating the column stepwise with PB 0.03 M pH 6.0, 0.045 M pH 6.25, 0.06 M pH 6.5 and 0.12 M pH 7.2. The fractions containing the enterotoxin are combined, concentrated with polyethylene glycol (200 ml wet volume of packed resin), and dialyzed against 0.5 M NaCl 0.05 M PB pH 7.2. The concentrated enterotoxin solution (5 ml) is placed in a column of Sephacryl S-200 (pretreated with 0.5 M NaCl, 0.05 M PB, pH 7.2). The column is eluted with the same buffer. The fractions containing the enterotoxin are combined and dialyzed against 0.01 M PB, 0.15 M NaCl pH 7.2. The enterotoxin B concentration is approximately 1 mg/ml. The solution is filter sterilized, frozen and lyophilized. Samples are stored in lyophilized form at 4° C. The final enterotoxin fraction is a white powder which, when dissolved in normal saline, is a clear colorless solution. Samples containing 5 and 10 μg/ml are tested in a double diffusion immunoprecipitation assay using known standards of SEB and mono-specific antisera. A single precipitation line is noted which showed a line of identity with known SEB. Using a tritiated thymidine mitogenic assay with human and murine immunocytes, SEB showed significant mitogenic activity comparable to that of SEA. SEB was found to be devoid of contaminating alpha hemolysin assessed in a rabbit erythrocyte hemolytic assay.

PAGE gel analysis of SEB showed a predominant single band at 28,000 m.w. High performance liquid chromatography (HPLC) profiles were obtained on a MAC PLUS controlling a Rainin Rabbit HPLC with a Hewlett Packard 1040 A Diode array detector and a Vyadac Protein and Peptide C18 column. The profile for purified enterotoxin B was a sharp peak without significant shoulder. There was minimal trace contamination. Amino acid analysis was carried out with a Bechman 6300 amino acid analyzer and displayed residues consistent with known SEB standards. The sterility of the preparations was demonstrated by negative cultures in thioglycolate medium and soybean-casein digest. Protein determinations were carried out by a spectrophotometric method.

The sterility of the preparation was demonstrated by negative cultures using (a) fluid thioglycollate medium and (b) soybean-casein digest. A sample containing 1 mg/ml of SEB was tested for endotoxin contamination using Sigma E-toxate LAL assay. The final product was found to be free of endotoxin with a standard sensitivity of 0.1 ug endotoxin/mg SEB.

Toxicity testing was carried out in two Hartley strain guinea pigs weighing less than 450 grams, and two female C57 black mice (Simonson Laboratories, Watsonville, Calif.), weighing less than 22 grams. Each animal was observed for 7 days with no significant change in condition or weight after intraperitoneal injection of 0.5 ml of 26 μg/kg enterotoxin B.

SEA, SEC, SED, SEE, TSST-1 and Streptococcal pyrogenic exotoxin in the studies were prepared by the previously described methods. The identity, purity and sterility of these preparations were tested in a fashion similar to that for SEB.

EXAMPLE 6

Isolation Of Host Cells: Lymph Nodes

As noted previously, the invention involves, in one embodiment, a method wherein host cells are removed and stimulated outside the body, i.e., ex vivo, with stimulating antigens. These cells may be isolated from a variety of sources. In this example, they are obtained from the lymph nodes.

Inguinal, mesenteric, or superficial distal axillary lymph nodes are removed aseptically. Single cell suspensions are prepared by teasing (e.g., with 20-gauge needles) followed by pressing mechanically with the blunt end of a 10-ml plastic syringe plunger in buffer under sterile conditions. The cell preparations were filtered through a layer of No. 100 nylon mesh (Nytex; TETKO Inc., Elmsford, N.Y.), centrifuged and washed. Red cells, if evident, are lysed by treatment with ammonium chloride-potassium lysing buffer (8.29 g $NH_4Cl$, 1.0 g $KHCO_3$, and 0.0372 g EDTA/liter, pH 7.4). The cells were washed twice with buffer and resuspended for stimulation.

EXAMPLE 7

Isolation Of Host Cells: Spleen Cells

In this example, the host cells are obtained from the human spleen. Either a left subcostal incision or midline incision may be used for resection. The spleen is mobilized initially by dividing the ligamentous attachments, which are usually avascular. The short gastric vessels then are doubly ligated and transected. This permits ultimate dissection of the splenic hilus with individual ligation and division of the splenic artery and vein.

The sequence of technical maneuvers necessary to remove the spleen varies somewhat, depending on the surgeon's election to approach the splenic hilum either anteriorly or posteriorly. The anterior approach is somewhat slower.

Anterior Method. On entering the abdomen, the stomach should be thoroughly emptied by suction through a nasogastric tube already in place, if this maneuver has not been accomplished preoperatively. An opening is made in the gastrosplenic omentum in an avascular area, and by retracting the stomach upward and anteriorly through this opening the upper part of the pancreas can be visualized. The tortuous splenic artery can be seen along its upper margin; it is, at the option of the surgeon, ligated.

The next step in the procedure is division of the lower two-thirds of the gastrosplenic omentum. This is accomplished by dividing the vascular omentum between clamps and ligating the cut ends subsequently. The gastrosplenic omentum is frequently infiltrated with a considerable amount of adipose tissue and tends to slip away from clamps, especially if traction is applied to the instruments. The upper portion of this omentum also contains the vasa brevia and large venous tributaries joining the left gastro-epiploic vein. To avoid hemorrhage from these sources, suture ligation rather than simple ligatures should be utilized in this area. Access to the upper portion of the gastrosplenic omentum is difficult with the spleen in situ, and for this reason it is best divided with the later stage after mobilization of the splenic hilum.

Following division of the splenic vasculature, the splenorenal, the splenocolic, and the splenophrenic ligaments are divided. All except the last mentioned are generally avascular and pose no particular technical problems in division. The remnants of the splenophrenic ligament left behind may have to be underrun with running chromic catgut suture for hemostasis. The spleen is displaced from the abdomen and delivered through the incision. The only remaining attachments still in place is the upper third of the gastrosplenic ligament which is now carefully divided between ligatures, completing the splenectomy procedure.

Posterior Method. The posterior approach of removing the spleen is much more expeditious than the anterior approach, but blood loss is usually more substantial than in the anterior approach. After entering the abdomen the surgeon makes an incision in the avascular splenorenal ligament and then inserts three fingers behind the hilum of the spleen which is easily mobilized by blind dissection. Hemorrhage from the splenic hilum during this process can be avoided by placing the incision on the splenorenal ligament closer to the kidney and away from the spleen. By rapidly dividing the splenophrenic and the splenocolic ligaments, it is now possible to deliver the spleen through the incision. Any hemorrhage from the splenic hilum or from the ruptured spleen itself is very easily controlled at this point by manual compression of the splenic hilum or placement of a noncrushing clamp, taking care not to injure the tail of the pancreas. The gastrosplenic ligament and the presplenic fold when present can now be divided and suture ligated in a deliberate manner.

Cell Suspensions. Spleen cells are mechanically dissociated by using the blunt end of a 10-ml plastic syringe in buffer. The cell suspension was passed through a single layer of 100-gauge nylon mesh (Nitex; Lawshe Industrial Co., Bethesda, Md.) and centrifuged, and the RBC lysed by resuspension of the cell pellet in ammonium chloride/potassium lysing buffer, (8.29 g of $NH_4Cl$, 1.0 g $KHCO_3$ and 0.0372 g of EDTA/L pH 7.4; Media Production Section, National Institutes of Health, Bethesda, Md.). The cells were again filtered through nylon mesh, washed two times, and resuspended in culture medium (see below).

EXAMPLE 8

Isolation Of Host Cells: Infiltrating Cells

In this example, the host cells are obtained from tumor infiltrating lymphocytes. Lymphocytes infiltrating tumors are obtained using standard techniques. Solid tumors (freshly resected or cryopreserved) are dispersed into single cell suspensions by overnight enzymatic digestion [e.g., stirring overnight at room temperature in RPMI 1640 medium containing 0.01% hyaluronidase type V, 0.002% DNAse type I, 0.1% collagenase type IV (Sigman, St. Louis), and antibiotics]. Tumor suspensions are then passed over Ficoll-Hypaque gradients (Lymphocyte Separation Medium, Organon Teknika Corp., Durham, N.C.). The gradient interfaces contain viable tumor cells and mononuclear cells are washed, adjusted to a total cell concentration of 2.5 to $5.0 \times 10^5$ cells/ml and cultured in complete medium. Complete medium comprises RPMI 1640 with 10% heat-inactivated type-compatible human serum, penicillin 50 IU/ml and streptomycin 50 $\mu$g/ml (Biofluids, Rockville, Md.), gentamicin 50 $\mu$g/ml (GIBCO Laboratories, Chagrin Falls, Ohio), amphotericin 250 ng/ml (Funglzone, Squibb, Flow Laboratories, McLean, Va.), HEPES buffer 10 mM (Biofluids), and L-glutamine 2 mM (MA Bioproducts, Walkersville, Md.). Conditioned medium from 3- to 4-day autologous or allogeneic lymphokine-activated killer (LAK) cell cultures (see below) can be added at a final concentration of 20% (v/v). Recombinany IL-2 (kindly supplied by the Cetus Corporation, Emeryville, Calif.) can be added at a final concentration of 1000 $\mu$/ml.

Cultures are maintained at 37° C. in a 5% $CO_2$-humidified atmosphere. A variety of tissue culture vessels can be employed, including 24-well plates (Costar, Cambridge, Mass.). 175 $cm^2$ flasks (Falcon; Becton Dickinson, Oxnard, Calif.), 850 $cm^2$ roller bottles (Corning Glass Works, Corning, N.Y.), and 750 $cm^2$ gas-permeable culture bags (Fenwal Laboratories, Division of Travenol Laboratories, Deerfield, Ill.). Cultures should be fed weekly by harvesting, pelletting and resuspending cells at $2.5 \times 10^6$ cells/ml in fresh medium. Over an initial period (e.g., 2 to 3 weeks) of culture, the lymphocytes will selectively proliferate, while the remaining tumor cells will typically disappear completely.

To make LAK cell cultures, peripheral blood lymphocytes (PBL) are obtained from patients or normal donors. After passage over Ficoll-Hypaque gradients, cells are cultured at a concentration of $1 \times 10^6$ /ml in RPMI 1640 medium with 2% human serum, antibiotics, glutamine, and HEPES buffer. Recombinant IL-2 is added at 1000 $\mu$/ml. Cultures are maintained for 3 to 7 days in a humidified 5% $CO_2$ atmosphere at 37° C.

EXAMPLE 9

Ex Vivo Stimulation

This example describes an approach to stimulate host cells in vitro with superantigens for reinfusion. Tumor-draining lymph node (LN) cells are obtained as described in Example 7 and stimulated in vitro in a procedure with an optional second step.

Step One. For stimulation, $4 \times 10^6$ LN cells, in 2 ml of culture medium containing SEA or SEB, are incubated in a well of 24-well plates at 37° C. in a 5% $CO_2$ atmosphere for 2 days. The culture media comprises RPMI 1640 medium supplemented with 10% heat inactivated fetal calf serum, 0.1 mM nonessential amino acids, 1 $\mu$M sodium pyruvate, 2 mM freshly prepared L-glutamine, 100 $\mu$g/ml streptomycin, 100 U/ml penicillin, 50 $\mu$g/ml gentamicin, 0.5 $\mu$g/ml fungizone (all from GIBCO, Grand Island, N.Y.) and $5 \times 10^{-5}$ M 2-ME (Sigma). The cells were harvested and washed.

Step Two. The initially stimulated cells are further cultured at $3 \times 10^5$/well in 2 ml of culture media with Human recombinant IL-2 (available from Chiron Corp., Emeryville, Calif.; specific activity of 6 to 8×10⁶ U/mg protein; units equivalent to 2–3 International U). After 3 days incubation in IL-2, the cells can be collected, washed, counted to determine the degree of proliferation, and resuspended in media suitable for intravenous (i.v.) administration (e.g., physiological buffered saline solutions).

EXAMPLE 10

Immunotherapy

As noted previously, the present invention involves stimulating cells ex vivo, allowing them to differentiate into tumor specific immune effector cells. The cells are then reintroduced into the same host to mediate anticancer therapeutic effects.

In this example, 8 to 12 week old female C57BL/6J (B6) mice (Jackson Laboratory, Bar Harbor, Me.) are injected i.v. with approximately 3×10⁵ MCA 205 tumor cells (i.e., methylcholanthrene-induced tumors of B6 origin provided by Dr. James Yang, Surgery Branch, National Cancer Institute, Bethesda, Md.) suspended in 1 ml of media to initiate pulmonary metastases. These tumors can be routinely passed in vivo in syngeneic mice and used within the third to seventh transplantation generation.

On day 3, cells obtained from the mice as in Example 6 are stimulated ex vivo as in Example 9. Specifically, LN cells draining progressively growing MCA 205 fibrosarcoma for 12 d are stimulated with graded concentrations of SEA or SEB for 2 d followed by culture in 4 U/ml of IL-2 for 3 d.

The antitumor efficacy of superantigen stimulated cells is assessed by reinfusion. Mice may also be treated with exogenous IL-2 to promote the growth of transferred cells (i.p, with 15,000 U IL-2 in 0.5 ml buffered saline twice daily for 4 consecutive days to promote the in vivo function and survival of the stimulated cells). On day 20 or 21, all mice can be randomized, sacrificed, and metastatic tumor nodules on the surface of the lungs enumerated.

To identify Vβ phenotypes of cells in the tumor-draining LN before and after SEA and SEB stimulation, cells can be stained with a collection of anti-Vβ mAb. A preferential stimulation of particular Vβ T cell subsets by different microbial superantigenic toxins would suggest the possibility of antigenic specificity of the responding T cells.

EXAMPLE 11

Immobilized Superantigens For Sustained Delivery After Plasma Perfusion

Previous studies have shown that enterotoxins are present in commercial preparations of protein A produced by either enzymatic digestion of whole bacteria or by secretion into culture media. Indeed, the IgG used in affinity chromatography to isolate protein A has now been shown to contain the complete library of antibodies to virtually all enterotoxins. Following perfusion with plasma, plasma products or whole blood over enterotoxins immobilized on biocompatible support matrices, enterotoxins are released whether they were immobilized via covalent or non-covalent binding.

Enterotoxins or superantigens may be immobilized by non-covalent or covalent methods such as adsorption or carboduimide on inert supports such as collodion charcoal or silica, as previously described (U.S. Pat. No. 5,091,091, issued Feb. 25, 1992 to Terman). After plasma or blood product perfusion, the bound enterotoxins are released in a graded fashion over a 15 minute to 3 hour period. Toxicity associated with this procedure has been described in detail previously (Terman, 1984) and is manageable with corticosteroids and occasionally with low dose dopamine infusions. Hence, the immobilized enterotoxins may represent another safe and effective mode of administration of enterotoxins to patients.

In this example, enterotoxins are provided for intravenous adminstration by displacement chromatography from immobilized surfaces after plasma or plasma component perfusion. Enterotoxins are immobilized on solid surfaces by carbodiimide chemistry or adsorbed by adsorptive chemistry on solid supports. Surfaces include silica, glass, cellulose, agarose, polystyrene and methacrylate. Perfused fluids can be selected from a group containing albumin, immunoglobulins or other plasma proteins. For covalent attachments, the carbodiimide may be incubated with enterotoxin before addition to the derivatized surface in order to prepolymerize the molecule. The solid support may be derivatized with a silanizing agent prior to addition of the polymerized enterotoxins. Other bifunctional agents may be used such as glutaraldehyde, etc. It is important that the binding of the enterotoxin to the solid support not be irreversible so as to interdict displacement of the bound protein by the perfused fluid.

Inert matrices such as glass, silica, agarose, polystyrene, polyacrylamide may be used. Examples of peptide binding using silica as the inert support and carbodiimide as the coupling agent are given below.

The silica is derivatized with the amino group as the reactive functional sites as follows:

(a) The silica is acid washed, followed by extensive rinsing with water and drying. The silica is then reacted with a 5–10% solution of aminosilane such as γ-aminopropyltriethoxysilane with pH adjusted to approximately 3.0 for 2 hours at 75° C. after which the matrix is again washed extensively with water and dried overnight at 100°.

(b) Carboxyl groups are introduced to the amino-derivatized material by mixing the silica matrix with succinic anhydride in a suitable buffer, such as 0.5M phospate buffer with pH adjusted to 6.0 and held for 12–16 hours at room temperature after which the matrix is extensively washed and dried.

(c) Hydroxyl groups may be added by addition of a silane such as γ-glycidoxylpropyltrimethoxysilane for 2 hours at 75° C. The silica matrix is then washed and dried at 100° C.

(d) The derivatized silica matrix may be reacted with enterotoxins in the presence of carbodiimide to form a covalent linkage. The binding reaction for the amino-derivatized matrix is as follows:

Enterotoxin is mixed in water in the presence of carbodiimide. The pH of the solution is adjusted to the range from 3.5 to 4.5, usually about 3.5, and the silica matrix is introduced and mixed for 5 to 30 hours at room temperature. The matrix is washed, dried and acid washed at pH 2.0 to 2.5 to remove labile protein and other substances noncovalently bound, followed by washing and drying.

(e) The binding process for carboxyl-derivatized silica is as follows: A carbodiimide is dissolved in water and the solution is adjusted to pH 3.5 to 4.5. The silica matrix is introduced and the solution is stirred for 10 to 25 hours at room temperature. The silica matrix is then removed and washed with water. The enterotoxins are then dissolved in water, pH adjusted to 3.5 to 4.5 and the silica matrix added and mixed for 15–30 hours. The silica matrix is then washed with water and dried, washed once in acid pH 2.0 to 2.5, then washed and dried.

Enterotoxins may be immobilized on inert solid surfaces by passive adsorption. Noncovalent coating may involve hydrophobic interactions, hydrogen bonds, ionic bonds, or protein-protein interactions. Inert surfaces for adsorption may include polystyrene balls or beads, silica, collagen or celluloric membranes. Noncovalent adsorption of proteins proceeds with little difficulty in a wide range of buffer conditions. The inert common procedures recommend 50 mM sodium carbonate at a pH between 9.2 and 9.6. However, a PBS buffer (10 mM sodium phosphate, 0.15 M NaCl), pH 7.2, or a TBS buffer (10 mM Tris, 0.15 M NaCl), pH 8.5 often works just as well. Components of buffers that compete for hydrophobic adsorption sites on plastic surfaces should be avoided. Detergents such as TRITON X-100, TWEEN 20 or NP-40 should be avoided since they will bind to the surface better than antibody molecules will. Coating should be done at 4° C. for at least 18 hours. At 37° C., the coating procedure may be complete within 90 minutes.

The method of adsorption is as follows:

1. An enterotoxin solution is prepared from purified enterotoxins at a concentration of 1–10 μg/ml in 50 mM sodium carbonate, pH 9.5. For a 96-well plate, a 20-ml solution will be sufficient to dispense 150 μl per well with enough extra solution to properly pipette with a multichannel pipetter. For coating polystyrene beads or balls, enough coating solution is made to fully immerse the balls in the antibody.
2. Antibody solution is added (150 μl) to each well of a microtiter plate. Alternatively, the polystyrene balls are submerged in the antibody solution.
3. The reaction is incubated at 4° C. for at least 18 hrs, or at 37° C. for at least 90 minutes.
4. The plates or balls are washed at least five times with PBS, pH 7.2, containing 0.05% TWEEN 20. Aliquots of 250 μl of each wash solution are added to the wells of the microplate. Beads or balls, are immersed in wash solution and incubated for several minutes. Then they are removed from the solution.

EXAMPLE 12

Preparation of Polymerized Enterotoxins And Antigen-Antibody Oligomers

Enterotoxins may be polymerized by incubation with several well known bifimctional agents such as glutaraldehyde, carbodiimide, and heterobifimctional agents such as sulfo-SMCC and the like. The resultant oligomers may then be separated on a size chromatography column, concentrated and stored for subsequent use.

Enterotoxin-antibody complexes can be prepared by incubation with various dilutions of antibodies. The resulting conjugates may be further separated by size gel chromatography and sucrose density gradients. Biological activity of the conjugates can be tested in murine and human T cell mitogenesis assays.

From the above, it should be clear that the present invention provides a method for the treatment of cancer, and, more specifically, for the treatment of solid tumors, including their metastases, without radiation, surgery or standard chemotherapeutic agents. The ex vivo stimulation method has decided advantages over direct intravenous injection of superantigens. Most importantly, success is achieved with minimal host toxicity.

What is claimed is:

1. A tumor cell comprising a first and a second exogenous nucleic acid molecule, wherein (a) said first exogenous nucleic acid molecule encodes a superantigen or a biologically active fragment of a superantigen, and (b) said second exogenous nucleic acid molecule encodes a co-stimulatory molecule that is characterized as activating T cells in conjunction with an antigenic stimulus, which first and second nucleic acid molecules are expressed in said cell, rendering said cell capable of stimulating antitumor immune reactivity in vitro or in vivo.

2. The cell of claim 1, which expresses an MHC class II molecule.

3. The cell of claim 2, wherein said MHC class II molecule is an HLA-DQ, an HLA-DR, or an HLA-DP molecule.

4. The cell of claim 1, wherein said superantigen is a staphylococcal enterotoxin.

5. The cell of claim 4, wherein said staphylococcal enterotoxin is selected from the group consisting of SEA, SEB, $SEC_1$, $SEC_2$, $SEC_3$, SED, SEE, and SEF.

6. The cell of claim 1, wherein said superantigen is a streptococcal pyrogenic exotoxin.

7. The cell of claim 6, wherein said streptococcal pyrogenic exotoxin is selected from the group consisting of SPEA, SPEB, and SPEC.

8. The cell of claim 1, wherein said superantigen is a toxic shock-associated toxin.

9. The cell of claim 8, wherein said toxic shock associated toxin is TSST1.

10. The cell of claim 1, wherein said superantigen is a *Staphylococcus aureus* exfoliating toxin.

11. The cell of claim 10, wherein said *Staphylococcus aureus* exfoliating toxin is selected from the group consisting of ETA and ETB.

12. The cell of claim 1, wherein said superantigen is a minor lymphocyte stimulating antigen.

13. The cell of claim 1, wherein said superantigen is a mycoplasma antigen.

14. The cell of claim 1, wherein said superantigen is a mnycobacterial antigen.

15. The cell of claim 1, wherein said superantigen is a Yersinia antigen.

16. The cell of claim 1, wherein said superantigen is a heat shock protein.

17. The cell of claim 1, wherein said superantigen is a stress peptide.

18. The cell of claim 1, wherein said superantigen is expressed on the surface of said cell.

19. The cell of claim 1 which comprises a third exogenous nucleic acid encoding an MHC class II molecule which is expressed in said cell.

20. The cell of claim 19, wherein said MHC class II molecule is an HLA-DQ, HLA-DR, or HLA-DP molecule.

21. The cell of claim 19 which comprises a fourth exogenous nucleic acid encoding an adhesion molecule which is expressed in said cell.

22. The cell of claim 1 which comprises a third exogenous nucleic acid encoding an adhesion molecule which is expressed in said cell.

23. The cell of claim 1, wherein said cell is from a tumor-bearing host.

24. The cell of claim 1, wherein said tumor-bearing host is a human.

25. The cell of any of claims 1, 19, 20, 21, or 22, wherein said co-stimulatory molecule is B7.

* * * * *